United States Patent [19]
Nelson et al.

[11] Patent Number: 5,508,681
[45] Date of Patent: Apr. 16, 1996

[54] INTERACTIVE SAFE FOR DISPOSAL OF MEDICAL NEEDLES

[75] Inventors: Mark Nelson, Sandy; David Vangeison, Salt Lake City; Phillip K. Evans, Murry; Robert Wells, Salt Lake City, all of Utah

[73] Assignee: Life Medical Technologies, Inc., Salt Lake City, Utah

[21] Appl. No.: 235,286

[22] Filed: Apr. 29, 1994

[51] Int. Cl.⁶ .................................................. G08B 21/00
[52] U.S. Cl. ............................ 340/540; 206/366; 604/110
[58] Field of Search ..................................... 340/540, 568, 340/556, 638, 636; 604/110–111; 206/366; 109/1 R, 23, 38; 232/43.2; 70/57; 377/6

[56] References Cited

U.S. PATENT DOCUMENTS

| | | | |
|---|---|---|---|
| 3,727,749 | 4/1973 | Martin | 206/366 |
| 4,989,307 | 2/1991 | Sharpe et al. | 206/366 X |
| 5,188,598 | 2/1993 | Thead et al. | 604/110 |
| 5,193,678 | 3/1993 | Janocik et al. | 206/366 X |
| 5,356,383 | 10/1994 | Daly et al. | 604/110 |
| 5,356,385 | 10/1994 | Latini | 604/110 |

*Primary Examiner*—Thomas Mullen
*Attorney, Agent, or Firm*—M. Reid Russell

[57] ABSTRACT

A closed automatic system for removing (for facilitating the removal) and safely storing potentially contaminated medical (or other) needles in which the operator only uses one hand to operate the system. The system has a counter which counts the number of actuations of the needle sensor. When a predetermined limit is reached the device signals the operator that the safe is nearly full. A further fixed number of needles can then be removed, when that limit is reached, a fuse on the safe is blown causing the system to be inoperative until a new box is installed. Removal of the box also causes the fuse to be blown and the circuit is disabled until a new box is inserted. The safe storage box contains a tab which when fixed in the locked position can not be opened except upon the application of substantial force with a tool. The system uses a Motorola 705 EPROM or similar microcontroller. (Motorola product literature is incorporated by reference herein.)

6 Claims, 4 Drawing Sheets

INTERACTIVE SAFE FOR DISPOSAL OF MEDICAL NEEDLES

BACKGROUND OF THE INVENTION

The present invention relates to the safe disposal of needles which may be contaminated by blood or other fluids. The needles for disposal are attached to syringes using rotatable connectors, typically, but not limited to, threaded luer lock or luer slip type. The present invention is filed the same day, has the same inventors as and is assigned to the same party as SYSTEM FOR FACILITATING THE REMOVAL AND SAFE DISPOSITION OF MEDICAL NEEDLES. That patent application, Ser. No. 08/235,388 with a filing date of Apr. 29, 1994, is the invention of Nelson, Vangeison, Evans and Wells and is incorporated by reference in this application as if it were fully set forth herein.

The SYSTEM FOR FACILITATING THE REMOVAL AND SAFE DISPOSITION OF MEDICAL NEEDLES invention relates to a system and structure for facilitating the removal of potentially contaminated needles and depositing them into a container in an operation which requires the operator to use only one hand and virtually no physical effort. The system and structure employ at least one electrically powered and controlled rotating device for removing the needles. The system uses feedback control sub-systems for operating and controlling the rotating device, for limiting the number of needles which can be placed in a single storage container and for positioning the needle receiver in a predetermined configuration. The present invention teaches a novel and inventive safe for mating with the system and forming a part of that system as well as being inventive in its own right.

The basic problem to be solved in the field is the safe disposal of used (possibly bloodborne pathogen contaminated) needles with as close to zero risk of needle contact with personnel who use the needles as is possible. Greater risk to personnel is present when the needle removal device requires two hands or one hand with significant physical force or significant manual dexterity such as when reinserting the needle into its protective sheath. Greater risk to personnel is also present when the needles are not placed in a tamper proof container or when the container can overfill. A device which signals its full condition is safer to users than one which is merely in a jammed (inoperative) condition without otherwise signalling its jammed or full status.

FIELD OF THE INVENTION

The present invention relates to the field of the automated safe handling of needles (often called "sharps" in the trade) attached to syringes. The present invention particularly relates to a novel safe for use with and forming a part of a feedback controlled system in which the operator need use only one hand and minimal physical effort and in which the needles are, when removed, deposited in a tamper proof box which cannot be overloaded and which will not permit further needle removal until the full container is removed. In addition, the system will sense the removal of a safe and not permit its reinsertion into the system.

DESCRIPTION OF THE PRIOR ART

The closest prior art known to the applicants is U.S. Pat. No. 5,188,598, to Thead et al. The Thead '598 patent discloses a needle remover which has a mechanical locking device for limiting the number of needles placed in the storage or disposal container. The locking structure made of a number of gears with rotation limiting cutouts is contained in the disposable container.

SUMMARY OF THE INVENTION

The present invention teaches a safe for use in a closed system for removing and safely storing potentially contaminated medical (or other) needles in which the operator only uses one hand to operate. The system is essentially wholly automatic after the needle or other "sharp" is inserted.

When a predetermined number of actuations (needles removed) is reached the device signals the operator that the safe is nearly full. A further fixed number of needles can then be removed. When that limit is reached, a fuse (acting functionally as a switch) on the safe is blown causing a signal to be sent to the microcontroller to signal the full condition of the safe and rendering the device inoperative. A new safe, with an integral fuse, is installed completing the circuit and thereby making the device operative. Removal of the safe also causes the fuse to be blown and the circuitry is disabled until a new safe with fuse is inserted. The safe contains a tab which when fixed in the locked position can not be opened except upon the application of substantial force with a tool.

DESCRIPTION OF THE PREFERRED EMBODIMENT

Figure 1:
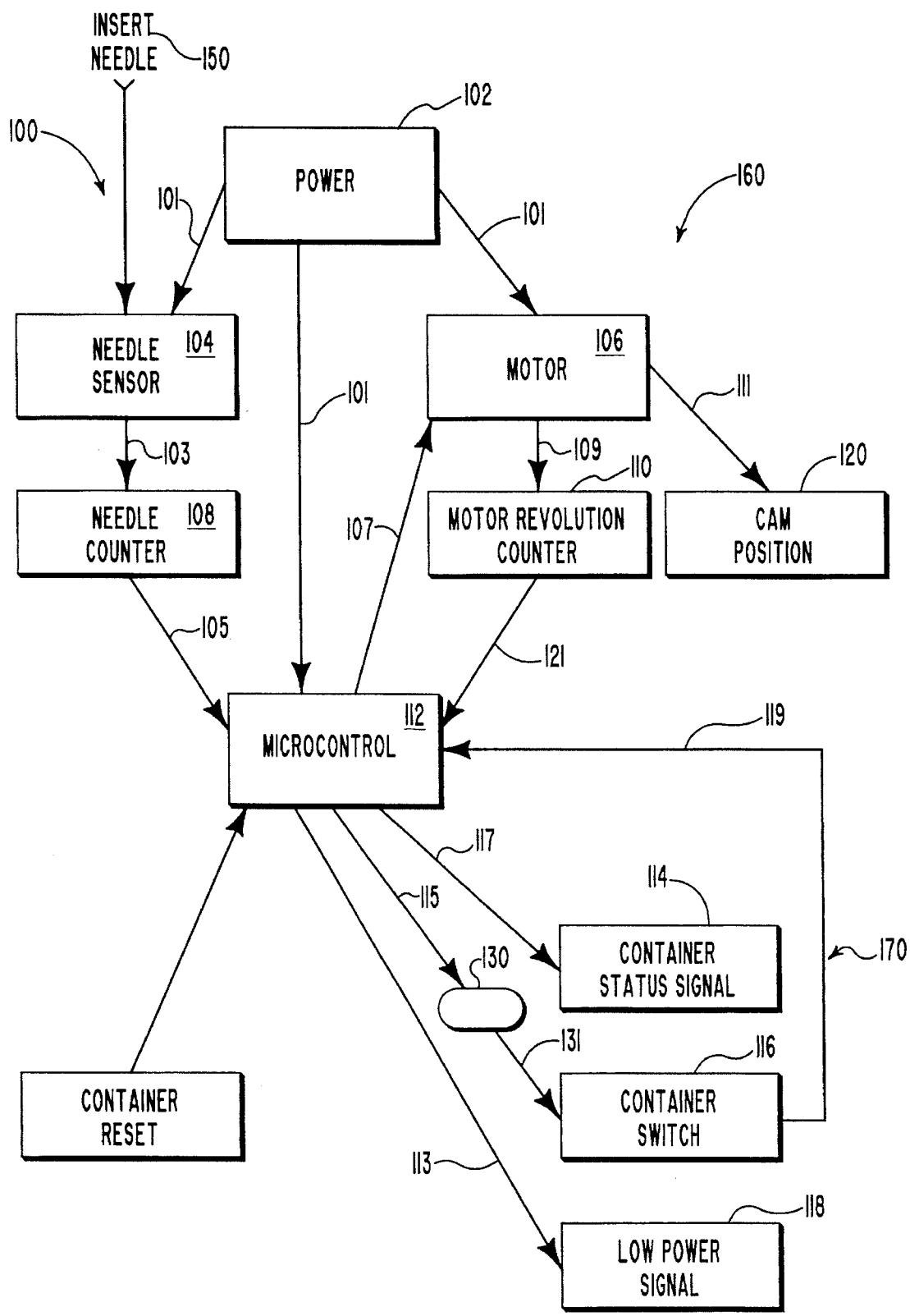
FIG. 1 shows a block diagram of the system of one embodiment of the present invention.

FIG. 1 is a block diagram of the first embodiment of the present invention showing the present invention generally by the number 100. A source of power 102 which can be from either an electrical outlet or from batteries is fed by wires 101 to a needle sensor 104, an electric motor 106 and an integrated circuit (microcontroller)112.

The needle sensor 104 is formed from a pair of light emitting and sensing diodes (or from an infra-red light emitting diode and photo transistor pair) which sense the presence of the needle by the interruption of the beam of light which may be pulsed infra-red light. The output of the needle sensor is fed by wire 103 to a first counter 108 which then counts the number of needles and provides a signal to a microcontroller 112 (that is preferably a Motorola 705 microprocessor which has a pre-determined program etched or burned in it). The output of the microcontroller is fed by wires 107, 113, 115, 117 to motor 106, low power sensor 118, energy storage device 130 (such as a capacitor) and by wire 131 to safe switch (fuse) 116 and container status signal 114.

The output of motor 106 is fed by wire 109 to second counter 110 whose output is fed by wire 121 back to microcontroller 112 to form a first feedback loop 160. A second feedback loop 170 is formed by wire 119 feeding the output of switch 116 back to microcontroller 112. The output of motor 106 is also fed by line 111 to drive gear 120 to control the actuation of the drive gears and cams and the final position of the gears and cams at the end of each cycle.

FIG. 1 shows the counter or counters as separate devices from the microcontroller. In practice, an integrated circuit or circuits will be used to constitute the microcontroller. Thus the counter or counters and feedback loops may be contained on one or more integrated circuit chips. The actual control of the micro-circuits may be obtained by fixing the operation of one or more so-called "eproms". It is well within the skill of the electrical engineers and art to use commercially available circuit elements to achieve the functions taught by the present invention without requiring any invention by the user.

Figure 2:
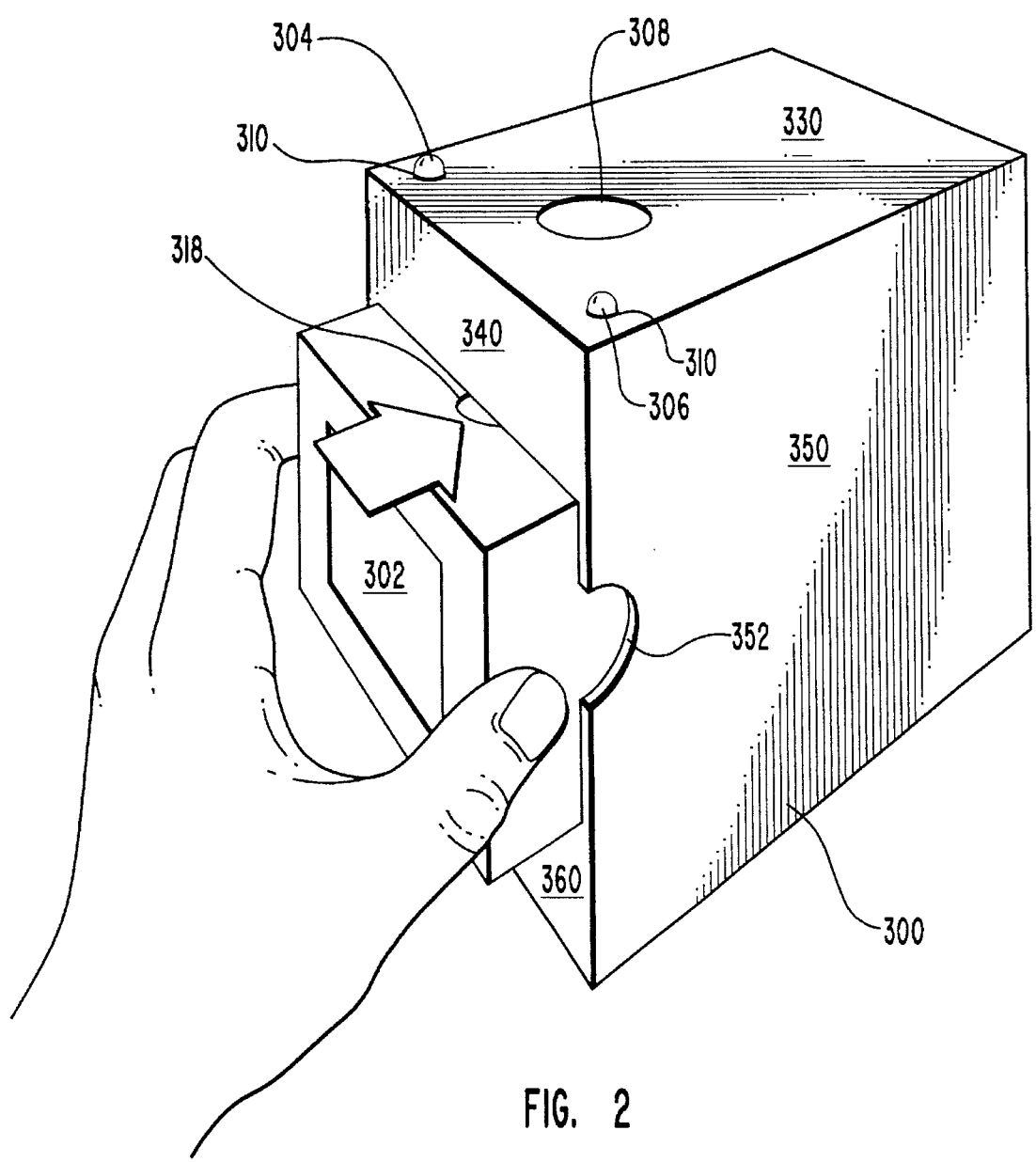
FIG. 2 is a front perspective of a part of an embodiment 300 of the present invention showing the removable needle storage box (safe) in FIG. 3.

The outer physical structure of a part of one embodiment of the present invention is shown in FIG. 2. An outer cover shown generally by 300 has side walls 350, a base section 360 and an upper section 340 with a top 330. The top has signal apertures 310 formed therein for permitting signal lights 304 and 306 to fit through. A needle aperture 308 is also formed in the top section 330.

A needle disposal container (safe) 302 has a closable needle receiver 318 formed therein which aligns with the needle aperture 308 formed in the box 300. Arcs 352 are formed in the sides 350 of the cover for making it easier to grasp the needle disposal box (safe).

Figure 3:
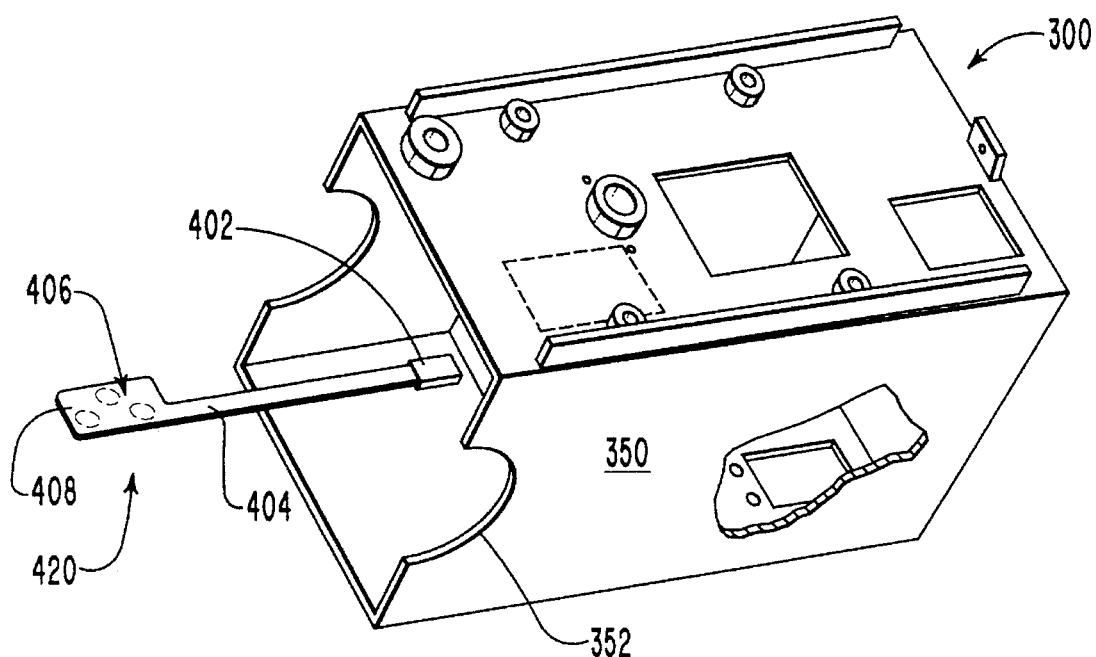
FIG. 3 shows a top perspective view of an embodiment of the present invention with the needle storage box (safe) removed in a partially disassembled view to show certain electrical connections.

FIG. 3 shows a view of the outer cover 300 in which an electrical connector 402 interconnects the other system circuit elements to a cable 404 which has an upper surface 406 and a lower surface 408. The surface 406 is fastened to a wall of the outer cover 300 to expose the lower surface 408 which is shown in more detail in FIG. 4.

Figure 4:
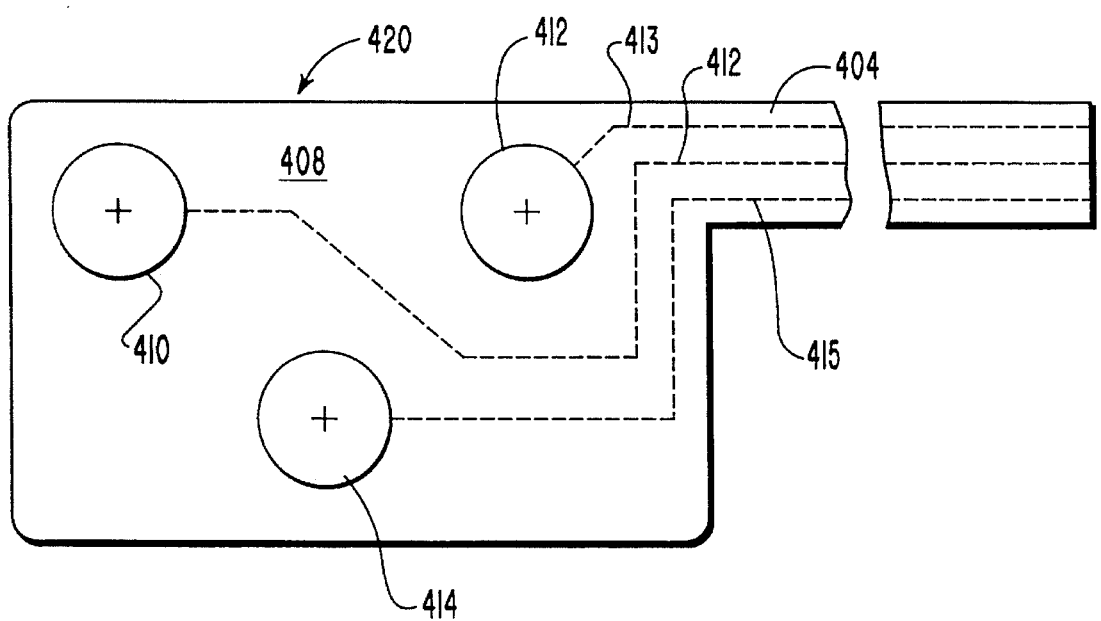
FIG. 4 shows a detailed view of the underside of an embodiment of the electrical connection shown in FIG. 3.

FIG. 4 shows that the lower surface 408 has three electrically conductive or contact pads (forming an array) 410, 412, and 414 connected to lead wires 411, 413, 415 for interconnecting the pad to the system circuitry through connector 402 shown in FIG. 3.

Figure 5:
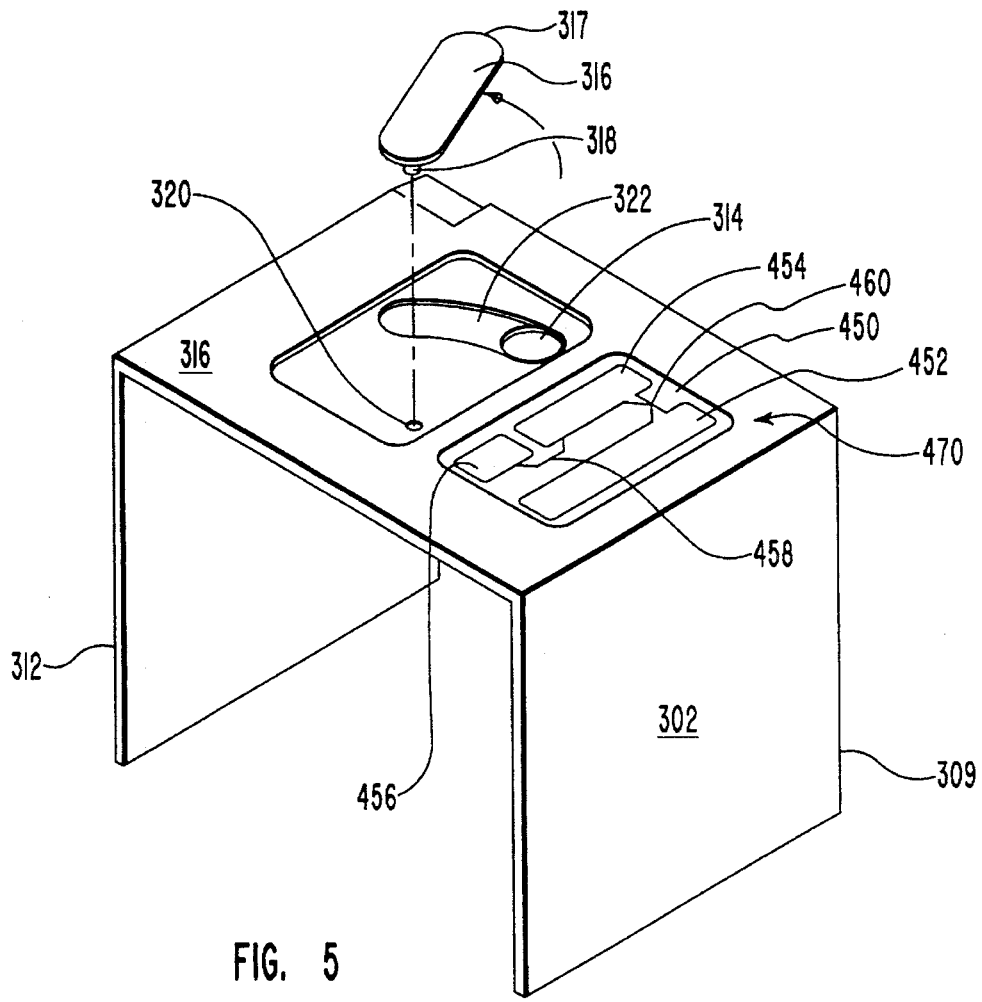
FIG. 5 shows a perspective view of a portion of the needle disposal box (safe) shown in FIG. 2 showing an embodiment of an electrical fuse (switch) forming a part of the invention.

FIG. 5 shows part of the safe (in one embodiment 302) having one of its "U" shaped members with three sides 309, 311 and 312. The upper surface 311 has an opening 314 which is aligned with opening 308 of the outer cover and a rotatable locking tab 316 having a locking end 317 which mates with receiver 322 and opening 308 to close and lock opening 314. A stubb shaft 318 mates with aperture 320 to permit rotation of the tab 316 about shaft 318.

A substrate 450 serves as a base for an electrically conductive pad 470 formed into a modified "X" shape having a first leg 452 and a second leg formed of two segments 454 and 456 interconnected to conductive line 458. Fuse segment 460 is formed to have a very thin cross section such that it will be melted or blown by a charge of stored energy from circuit element 130 shown in FIG. 1. The entire conductive pattern 470 may be screen printed onto the substrate 450 or laid down on top of safe 302 by any other suitable means.

Figure 6:
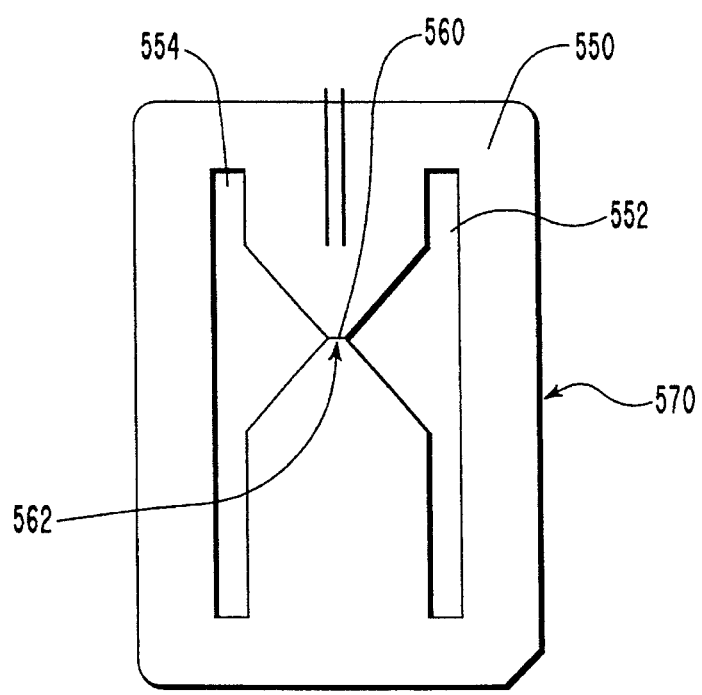
FIG. 6 shows a top view of an electrical fuse (switch) for use with the safe shown in FIG. 5 forming a part of another embodiment of the present invention.

An alternative conductive pad is shown in FIG. 6 in which like elements to FIG. 5 are shown by like numbers with only the hundreds place digit changed from a 4 to a 5.

Either embodiment of the safe conductive pad 470 or 570 mates with the conductive pad 420 such that when the safe 302 is inserted in the housing 300, contact pads 410, 412 and 414 mate with conductive segments 454, 456 and 452 respectively or segments 554 and 552 of the FIG. 6 embodiment. When the safe is removed and it is not full in the sense meant by the system, the extraction of the safe 302 far enough to remove contact pad 410 from a conductive segment will signal the microcontroller 112 which will cause the stored energy in capacitor 130 to discharge through line 131 and burn fuse element 460 or 560. The fuse element 562 is carefully chosen to burn at a current level which can be supplied by power source 102. This choice is one within the skill of the art.

The embodiments of the present invention which have been shown and described are illustrative of the main principles of the invention but the following claims shall not be limited to the embodiments shown. The claims are intended to cover and do cover those variations of the invention which are apparent to those skilled in the art.

We claim:

1. A safe for insertion into a needle removing apparatus for removing medical needles comprising:

a needle storage box means;

an opening formed in said needle storage box means for receiving removed needles;

a rotatable locking tab means connected to said storage box means for sealing said opening; and an electrically conductive pattern formed on a surface of said needle storage box means as a fuse means for melting to break an electrical circuit to a needle removing apparatus that said needle storage box means is inserted into on receipt of an electrical charge passed thereto from a microcontroller means of said needle storage box means upon a determination by said microcontroller means that said needle storage box means is full.

2. The safe claimed in claim 1 further including:

a switch means for interconnecting with said electrically conductive pattern formed on the surface of said storage box means to receive the electrical charge.

3. The safe claimed in claim 1 further including:

the electrically conductive pattern has formed therein a fusible segment as the fuse means for melting on receipt of a set level of electrical charge.

4. The safe claimed in claim 1 wherein: said electrically conductive pattern is adapted to mate with an electrically conductive pad that is electrically connected to said needle removing apparatus.

5. The safe claimed in claim 1 further including:

the electrically conductive pattern is formed on a top surface of the needle storage box means by screen printing said electrically conductive pattern thereon.

6. The safe claimed in claim 5 further including:

a fusible segment as the fuse means formed in the electrically conductive pattern that will melt on receipt of the electrical charge from the microcontroller means of the needle storage box means.

* * * * *